United States Patent
Wei et al.

(10) Patent No.: US 11,779,633 B2
(45) Date of Patent: Oct. 10, 2023

(54) GLUCAGON-LIKE PEPTIDE 1 RECEPTOR AGONISTS AND USES THEREOF

(71) Applicant: Regeneran Pharmaceuticals, Inc., Tarrytown, NY (US)

(72) Inventors: Yang Wei, Yorktown Heights, NY (US); Haruka Okamoto, New York, NY (US); Jesper Gromada, Scarsdale, NY (US); Samuel Davis, New York, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 77 days.

(21) Appl. No.: 17/332,215

(22) Filed: May 27, 2021

(65) Prior Publication Data
US 2021/0283225 A1    Sep. 16, 2021

Related U.S. Application Data

(62) Division of application No. 16/137,662, filed on Sep. 21, 2018, now Pat. No. 11,045,522.

(60) Provisional application No. 62/562,283, filed on Sep. 22, 2017.

(51) Int. Cl.
| | |
|---|---|
| *A61K 38/26* | (2006.01) |
| *C07K 16/28* | (2006.01) |
| *C07K 14/605* | (2006.01) |
| *A61P 3/04* | (2006.01) |
| *A61P 3/10* | (2006.01) |
| *A61K 31/155* | (2006.01) |
| *A61K 31/5415* | (2006.01) |
| *C07K 16/08* | (2006.01) |
| *C12N 15/62* | (2006.01) |
| *A61K 38/00* | (2006.01) |

(52) U.S. Cl.
CPC ............ *A61K 38/26* (2013.01); *A61K 31/155* (2013.01); *A61K 31/5415* (2013.01); *A61P 3/04* (2018.01); *A61P 3/10* (2018.01); *C07K 14/605* (2013.01); *C07K 16/082* (2013.01); *C07K 16/2869* (2013.01); *C12N 15/62* (2013.01); *A61K 38/00* (2013.01); *C07K 2319/00* (2013.01)

(58) Field of Classification Search
CPC .. A61K 38/26; A61K 31/155; A61K 31/5415; A61K 38/00; C07K 16/2869; C07K 14/605; C07K 16/082; C07K 2319/00; A61P 3/04; A61P 3/10; C12N 15/62
See application file for complete search history.

(56) References Cited

U.S. PATENT DOCUMENTS

| | | | |
|---|---|---|---|
| 7,452,966 B2 | 11/2008 | Glaesner et al. | |
| 7,833,531 B2 | 11/2010 | O'Neil et al. | |
| 8,389,689 B2 | 3/2013 | O'Neil et al. | |
| 8,497,240 B2 | 7/2013 | Levy et al. | |
| 8,557,769 B2 | 10/2013 | Coskun et al. | |
| 8,883,447 B2 | 11/2014 | O'Neil et al. | |
| 8,895,694 B2 | 11/2014 | Spetzler et al. | |
| 9,409,966 B2 | 8/2016 | Spetzler et al. | |
| 2006/0275288 A1 | 12/2006 | Grihalde et al. | |
| 2012/0148586 A1 | 6/2012 | Chou et al. | |
| 2014/0024586 A1 | 1/2014 | Coskun et al. | |
| 2014/0073563 A1 | 3/2014 | Boscheinen et al. | |
| 2015/0259416 A1 | 9/2015 | Berggren et al. | |
| 2015/0313908 A1 | 11/2015 | Mjalli et al. | |
| 2016/0194371 A1 | 7/2016 | Boscheinen et al. | |
| 2016/0361390 A1 | 12/2016 | Van Cauter | |
| 2017/0112904 A1 | 4/2017 | Alsina-Fernandez et al. | |
| 2017/0114115 A1 | 4/2017 | Alsina-Fernandez et al. | |

FOREIGN PATENT DOCUMENTS

| | | |
|---|---|---|
| CN | 104098702 A | 10/2014 |
| EP | 2470198 A2 | 7/2012 |
| EP | 3034514 A1 | 6/2016 |
| EP | 2373681 B1 | 1/2017 |
| KR | 101229610 B1 | 2/2013 |
| WO | 2014113357 A1 | 7/2014 |
| WO | 2015021871 A1 | 2/2015 |
| WO | 2016119399 A1 | 8/2016 |
| WO | 2016127887 A1 | 8/2016 |
| WO | 2017074715 A1 | 5/2017 |
| WO | 2017211922 A2 | 12/2017 |

OTHER PUBLICATIONS

Rojas et al, Metformin: an old but still the best treatment for type 2 diabetes, Diabetology & Metabolic Syndrome, 2013, 5, pp. 1-15.*
Joosten et al, The production of antibody fragments and antibody fusion proteins by yeasts and filamentous fungi, Microbial Cell Factories, 2003, 2, pp. 1-15.*
Oh et al., "Novel DPP-IV-resistant Analogs of GLP-1: The N-terminal Extension of GLP-1 by a Single Amino Acid" Korean Chem Soc. (2009), 30(10):2471-2474.
Al-Lazikani et al., "Standard conformations for the canonical structures of immunoglobulins.", J. Mol. Biol. 273:927-948 (1997).
Altschul et al. "Basic local alignment search tool.", (1990) J. Mol. Biol. 215: 403-410.

(Continued)

*Primary Examiner* — Li N Komatsu
(74) *Attorney, Agent, or Firm* — Fox Rothschild LLP; Thomas Triolo

(57) ABSTRACT

The present invention provides modified glucagon-like peptide 1 (GLP1) polypeptides, fusion proteins comprising modified GLP1 polypeptides, and methods of use thereof. In various embodiments of the invention, the fusion proteins are GLP1 receptor agonists that comprise a modified GLP1 fused to a stabilizing domain. In some embodiments, the fusion proteins comprising modified GLP1 are useful for treating or ameliorating a symptom or indication of a disorder such as obesity and diabetes.

5 Claims, No Drawings
Specification includes a Sequence Listing.

(56) References Cited

OTHER PUBLICATIONS

Altschul et al. "Gapped Blast and PSI-Blast: a new generation of protein database search programs.", (1997) Nucleic Acids Res. 25:3389-3402.
Manandhar et al., "Glucagon-like Peptide-1 (GLP-1) Analogs: Recent Advances, New Possibilities, and Therapeutic Implications", Journal of Medicinal Chemistry, vol. 58, No. 3, Feb. 12, 2015, pp. 1020-1037.
Butler, et al: "GLP-1-Based Therapy for Diabetes: What You Do Not Know Can Hurt You", Diabetes Care, Feb. 2010, vol. 33, No. 2, pp. 453-455.
Deacon et al, "Dipeptidyl peptidase IV resistant analogues of glucagon-like peptide-1 which have extended metabolic stability and improved biological activity.", 1998, Diabetologia 41: 271-278.
Gao, et al: "Development, Characterization, and Evaluation of a Fusion Protein of a Novel Glucagon-Like Peptide-1 (GLP-1) Analog and Human Serum Albumin inPichia Pastoris", Biosci. Biotechnol. Biochem., 73 (3), 688-694, 2009.
Garber, Alan J.: "Long-Acting Glucagon-Like Peptide 1 Receptor Agonists", Diabetes Care, May 2011, vol. 34, Suppl 2, pp. S279-S284.
Gonnet et al. "Exhaustive matching of the entire protein sequence database.", (1992) Science 256: 1443-45.
Chung et al., "The N-terminal alanine-extended GLP-1/IgG-Fc fusion protein confers resistance to DPP-IV and reduces serum glucose level in db/db mice", Regulatory Peptides, vol. 170, No. 1-3, Oct. 1, 2011, pp. 1-3.
International Search Report dated Feb. 25, 2019 for PCT/US2018/052110.
Langer, "New methods of drug delivery," (1990) Science 249:1527-1533.
Martin et al., "Modeling antibody hypervariable loops: A combined algorithm," Proc. Natl. Acad. Sci. USA 86:9268-9272 (1989).
NPL_Machine Translation of WO2016119399A-1, Aug. 4, 2016, pp. 1-42, accessed Apr. 8, 2019.
Padlan et al. "Identification of specificity-determining residues in antibodies," 1995 FASEB J. 9:133-139.
Pearson, "Using the FASTA program to search protein and DNA sequence databases," (1994) Methods Mol. Biol. 24: 307-331.
Powell et al. "Compendium of excipients for parenteral formulations" PDA (1998) J Pharm Sci Technol 52:238-311.
Reid, Timothy S.: "Practical Use of Glucagon-Llike Peptide-1 Receptor Agonist Therapy in Primary Care", Clinical Diabetes, Nov. 4, 2013, vol. 31, pp. 148-157.
Skugor, Mario: "Diabetes Mellitus Treatment", Medical Treatment of Diabetes Mellitus, Sep. 2016, [Retrieved from the Internet: <http://www.clevelandandclinicmeded.com/medicalpubs/diseasemanagement/endocrinology/diabetes-mellitus-treatment/>, pp. 1-15.
Tomkin, Gerald H.: "Treatment of Type 2 Diabetes, Lifestyle, GLP1 Agonists and DPP4 Inhibitors", World Journal of Diabetes, Oct. 15, 2014, vol. 5, No. 5, pp. 636-650.
Vajdos et al. "Comprehensive functional maps of the antigen-binding site of an anti-ErbB2 antibody obtained with shotgun scanning mutagenesis," 2002 J Mol Biol 320:415-428.
Glaesner et al., "Engineering and characterization of the long-acting glucagon-like peptide-1 analogue LY2189265, an Fc fusion protein", Diabetes/Metabolism Research and Reviews, vol. 26, No. 4, Apr. 30, 2010, pp. 287-296.
Written Opinion of the International Searching Authority dated Feb. 25, 2019 for PCT/US2018/052110.
Wu et al. "Receptor-mediated in vitro gene transformation by a soluble DNA carrier system," (1987) J. Biol. Chem. 262:4429-4432.
Kim et al., "Novel AGLP-1 albumin fusion protein as a long-lasting agent for type 2 diabetes," BMB Reports, vol. 46, No. 12, Dec. 31, 2013, pp. 606-610.

* cited by examiner

SEQUENCE LISTING

<160> NUMBER OF SEQ ID NOS: 14

<210> SEQ ID NO 1
<211> LENGTH: 120
<212> TYPE: PRT
<213> ORGANISM: Artificial Sequence
<220> FEATURE:
<223> OTHER INFORMATION: VH for Comparator

<400> SEQUENCE: 1

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Thr Gly Val Gly Trp Ile Arg Gln Pro Ser Gly Lys Gly Leu Glu
        35                  40                  45

```
Trp Leu Ser His Ile Trp Trp Asp Asp Val Lys Arg Tyr Asn Pro Ala
    50                  55                  60
Leu Lys Ser Arg Leu Thr Ile Ser Arg Asp Thr Ser Tyr Ser Gln Val
65                  70                  75                  80
Phe Leu Arg Ile Ala Ser Val Asp Thr Ala Asp Thr Ala Thr Tyr Tyr
                85                  90                  95
Cys Ala Arg Ile Leu Asp Gly Thr Gly Pro Met Asp Tyr Trp Gly Gln
            100                 105                 110
Gly Thr Ser Val Thr Val Ser Ser
            115                 120

<210> SEQ ID NO 2
<211> LENGTH: 108
<212> TYPE: PRT
<213> ORGANISM: Artificial Sequence
<220> FEATURE:
<223> OTHER INFORMATION: VL for Comparator

<400> SEQUENCE: 2

Gln Ile Val Leu Thr Gln Ser Pro Ala Ile Met Ser Ala Ser Pro Gly
1               5                   10                  15
Glu Lys Val Thr Met Thr Cys Ser Ala Ser Ser Arg Val Thr Tyr Met
            20                  25                  30
His Trp Tyr Gln Gln Arg Ser Gly Thr Ser Pro Lys Arg Trp Ile Tyr
        35                  40                  45
Asp Thr Ser Lys Leu Ala Ser Gly Val Pro Ala Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Gly Asn Asn Pro Gln Tyr
                85                  90                  95
Thr Phe Gly Gly Gly Thr Arg Leu Glu Ile Lys Arg
            100                 105

<210> SEQ ID NO 3
<211> LENGTH: 37
<212> TYPE: PRT
<213> ORGANISM: Artificial Sequence
<220> FEATURE:
<223> OTHER INFORMATION: GLP1

<400> SEQUENCE: 3

His Asp Glu Phe Glu Arg His Ala Glu Gly Thr Phe Thr Ser Asp Val
1               5                   10                  15
Ser Ser Tyr Leu Glu Gly Gln Ala Ala Lys Glu Phe Ile Ala Trp Leu
            20                  25                  30
Val Lys Gly Arg Gly
            35

<210> SEQ ID NO 4
<211> LENGTH: 31
<212> TYPE: PRT
<213> ORGANISM: Artificial Sequence
<220> FEATURE:
<223> OTHER INFORMATION: Mature GLP1

<400> SEQUENCE: 4

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Gly
```

<210> SEQ ID NO 5
<211> LENGTH: 30
<212> TYPE: PRT
<213> ORGANISM: Artificial Sequence
<220> FEATURE:
<223> OTHER INFORMATION: Des-Ala-GLP1

<400> SEQUENCE: 5

```
His Glu Gly Thr Phe Thr Ser Asp Val Ser Ser Tyr Leu Glu Gly Gln
 1               5                  10                  15
Ala Ala Lys Glu Phe Ile Ala Trp Leu Val Lys Gly Arg Gly
            20                  25                  30
```

<210> SEQ ID NO 6
<211> LENGTH: 32
<212> TYPE: PRT
<213> ORGANISM: Artificial Sequence
<220> FEATURE:
<223> OTHER INFORMATION: Q-GLP1

<400> SEQUENCE: 6

```
Gln His Ala Glu Gly Thr Phe Thr Ser Asp Val Ser Ser Tyr Leu Glu
 1               5                  10                  15
Gly Gln Ala Ala Lys Glu Phe Ile Ala Trp Leu Val Lys Gly Arg Gly
            20                  25                  30
```

<210> SEQ ID NO 7
<211> LENGTH: 32
<212> TYPE: PRT
<213> ORGANISM: Artificial Sequence
<220> FEATURE:
<223> OTHER INFORMATION: A-GLP1

<400> SEQUENCE: 7

```
Ala His Ala Glu Gly Thr Phe Thr Ser Asp Val Ser Ser Tyr Leu Glu
 1               5                  10                  15
Gly Gln Ala Ala Lys Glu Phe Ile Ala Trp Leu Val Lys Gly Arg Gly
            20                  25                  30
```

<210> SEQ ID NO 8
<211> LENGTH: 30
<212> TYPE: PRT
<213> ORGANISM: Artificial Sequence
<220> FEATURE:
<223> OTHER INFORMATION: des-H-GLP1

<400> SEQUENCE: 8

```
Ala Glu Gly Thr Phe Thr Ser Asp Val Ser Ser Tyr Leu Glu Gly Gln
 1               5                  10                  15
Ala Ala Lys Glu Phe Ile Ala Trp Leu Val Lys Gly Arg Gly
            20                  25                  30
```

<210> SEQ ID NO 9
<211> LENGTH: 273
<212> TYPE: PRT
<213> ORGANISM: Artificial Sequence
<220> FEATURE:
<223> OTHER INFORMATION: GLP1-3xG4S-hFc

<400> SEQUENCE: 9

```
His Ala Glu Gly Thr Phe Thr Ser Asp Val Ser Ser Tyr Leu Glu Gly
 1               5                  10                  15
```

Gln Ala Ala Lys Glu Phe Ile Ala Trp Leu Val Lys Gly Arg Gly
            20                  25                  30

Gly Gly Gly Ser Gly Gly Gly Ser Gly Gly Gly Ser Asp Lys
        35                  40                  45

Thr His Thr Cys Pro Pro Cys Pro Ala Pro Glu Leu Leu Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser His Glu Asp
                85                  90                  95

Pro Glu Val Lys Phe Asn Trp Tyr Val Asp Gly Val Glu Val His Asn
            100                 105                 110

Ala Lys Thr Lys Pro Arg Glu Glu Gln Tyr Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Ala Leu Pro Ala Pro Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Arg Asp Glu Leu Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Lys Leu Thr Val Asp Lys
225                 230                 235                 240

Ser Arg Trp Gln Gln Gly Asn Val Phe Ser Cys Ser Val Met His Glu
                245                 250                 255

Ala Leu His Asn His Tyr Thr Gln Lys Ser Leu Ser Leu Ser Pro Gly
            260                 265                 270

Lys

<210> SEQ ID NO 10
<211> LENGTH: 274
<212> TYPE: PRT
<213> ORGANISM: Artificial Sequence
<220> FEATURE:
<223> OTHER INFORMATION: A-GLP1-3xG4S-hFc

<400> SEQUENCE: 10

Ala His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

Gly Gly Gly Gly Ser Gly Gly Gly Ser Gly Gly Gly Ser Asp
        35                  40                  45

Lys Thr His Thr Cys Pro Pro Cys Pro Ala Pro Glu Leu Leu Gly Gly
    50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His

-continued

```
            100                 105                 110
Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Asp Glu Leu Thr Lys Asn Gln Val Ser Leu
            180                 185                 190

Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Lys

<210> SEQ ID NO 11
<211> LENGTH: 274
<212> TYPE: PRT
<213> ORGANISM: Artificial Sequence
<220> FEATURE:
<223> OTHER INFORMATION: Q-GLP1-3xG4S-hFc

<400> SEQUENCE: 11

Gln His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

Gly Gly Gly Gly Ser Gly Gly Gly Ser Gly Gly Gly Gly Ser Asp
        35                  40                  45

Lys Thr His Thr Cys Pro Pro Cys Pro Ala Pro Glu Leu Leu Gly Gly
    50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
            100                 105                 110

Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Asp Glu Leu Thr Lys Asn Gln Val Ser Leu
            180                 185                 190
```

```
Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
        245                 250                 255

Glu Ala Leu His Asn His Tyr Thr Gln Lys Ser Leu Ser Leu Ser Pro
        260                 265                 270

Gly Lys

<210> SEQ ID NO 12
<211> LENGTH: 272
<212> TYPE: PRT
<213> ORGANISM: Artificial Sequence
<220> FEATURE:
<223> OTHER INFORMATION: Des-Ala-GLP1-3xG4S-hFc

<400> SEQUENCE: 12

His Glu Gly Thr Phe Thr Ser Asp Val Ser Ser Tyr Leu Glu Gly Gln
1               5                   10                  15

Ala Ala Lys Glu Phe Ile Ala Trp Leu Val Lys Gly Arg Gly Gly Gly
            20                  25                  30

Gly Ser Gly Gly Gly Gly Ser Gly Gly Gly Gly Ser Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Asp Glu Leu Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270
```

<210> SEQ ID NO 13
<211> LENGTH: 272
<212> TYPE: PRT
<213> ORGANISM: Artificial Sequence
<220> FEATURE:
<223> OTHER INFORMATION: Des-H-GLP1-3xG4S-hFc

<400> SEQUENCE: 13

```
Ala Glu Gly Thr Phe Thr Ser Asp Val Ser Ser Tyr Leu Glu Gly Gln
1               5                   10                  15

Ala Ala Lys Glu Phe Ile Ala Trp Leu Val Lys Gly Arg Gly Gly Gly
            20                  25                  30

Gly Gly Ser Gly Gly Gly Gly Ser Gly Gly Gly Ser Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Asp Glu Leu Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270
```

<210> SEQ ID NO 14
<211> LENGTH: 276
<212> TYPE: PRT
<213> ORGANISM: Artificial Sequence
<220> FEATURE:
<223> OTHER INFORMATION: Comparator

<400> SEQUENCE: 14

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Gly Ser Ala Glu
        35                  40                  45
```

```
Ser Lys Tyr Gly Pro Pro Cys Pro Pro Cys Pro Ala Pro Glu Ala Ala
    50              55                  60

Gly Gly Pro Ser Val Phe Leu Phe Pro Pro Lys Pro Lys Asp Thr Leu
65              70                  75                      80

Met Ile Ser Arg Thr Pro Glu Val Thr Cys Val Val Val Asp Val Ser
            85                  90                  95

Gln Glu Asp Pro Glu Val Gln Phe Asn Trp Tyr Val Asp Gly Val Glu
            100             105             110

Val His Asn Ala Lys Thr Lys Pro Arg Glu Glu Gln Phe Asn Ser Thr
        115             120             125

Tyr Arg Val Val Ser Val Leu Thr Val Leu His Gln Asp Trp Leu Asn
    130             135             140

Gly Lys Glu Tyr Lys Cys Lys Val Ser Asn Lys Gly Leu Pro Ser Ser
145             150             155             160

Ile Glu Lys Thr Ile Ser Lys Ala Lys Gly Gln Pro Arg Glu Pro Gln
            165             170             175

Val Tyr Thr Leu Pro Pro Ser Gln Glu Glu Met Thr Lys Asn Gln Val
            180             185             190

Ser Leu Thr Cys Leu Val Lys Gly Phe Tyr Pro Ser Asp Ile Ala Val
        195             200             205

Glu Trp Glu Ser Asn Gly Gln Pro Glu Asn Asn Tyr Lys Thr Thr Pro
    210             215             220

Pro Val Leu Asp Ser Asp Gly Ser Phe Phe Leu Tyr Ser Arg Leu Thr
225             230             235             240

Val Asp Lys Ser Arg Trp Gln Glu Gly Asn Val Phe Ser Cys Ser Val
            245             250             255

Met His Glu Ala Leu His Asn His Tyr Thr Gln Lys Ser Leu Ser Leu
            260             265             270

Ser Leu Gly Lys
        275
```

GLUCAGON-LIKE PEPTIDE 1 RECEPTOR AGONISTS AND USES THEREOF

This application is a divisional of U.S. patent application Ser. No. 16/137,662 filed Sep. 21, 2018 (now U.S. Pat. No. 11,045,522), which claims the benefit of priority to U.S. Provisional Patent Application No. 62/562,283 filed Sep. 22, 2017, the disclosures of which are hereby incorporated by reference in their entireties.

FIELD OF THE INVENTION

The present invention is related to human glucagon-like peptide 1 receptor agonists, and therapeutic methods of using said agonists.

BACKGROUND OF THE INVENTION

Obesity has become a major health issue in the United States with two out of three Americans considered to be overweight or obese. Obesity is an important underlying risk factor for developing other diseases such as heart disease, stroke, and diabetes. Even a modest decrease in body weight (5-10% of initial body weight) lowers the risk for developing obesity-associated diseases such as heart disease and diabetes.

Diabetes mellitus is a chronic condition that is characterized by high blood sugar levels, and insulin resistance. If left untreated, the high blood sugar levels can lead to long-term complications including heart disease, stroke, diabetic retinopathy, and lower limb amputation. Treatment of diabetes involves controlling and reducing blood sugar levels and includes exercise and diet modification along with medications such as insulin and metformin.

One of the approaches used for treating obesity and for glycemic control involves glucagon-like peptide (GLP)-1 receptor agonists that target the incretin pathway. Glucagon-like peptide (GLP)-1 is a peptide hormone secreted by intestinal enteroendocrine cells. Upon oral glucose administration, GLP1 binds to its receptor leading to insulin secretion and a decrease in blood sugar levels (incretin effect). However, GLP1 is rapidly inactivated and degraded by the enzyme dipeptidyl peptidase 4 (DPP4) and has a very short half-life of 1.5 minutes. Longer-acting derivatives of GLP1 as well as GLP1 receptor agonists including fusion proteins comprising GLP1 have, therefore, been studied for diabetes control. GLP1 analogues, fusion proteins and GLP1 receptor agonists are disclosed, for example, in U.S. Pat. Nos. 7,452,966, 8,389,689, 8,497,240, 8,557,769, 8,883,447, 8,895,694, 9,409,966, US20160194371, US20140024586, US20140073563, US20120148586, US20170114115, US20170112904, US20160361390, US20150313908, US20150259416, WO2017074715, WO2016127887, WO2015021871, WO2014113357, EP3034514, EP2470198, and EP2373681.

However, there is a need for novel GLP1 peptide variants and GLP1 receptor agonists that are resistant to degradation by DPP4, have improved pharmacokinetic properties and have increased potency and sustained in vivo activity in glycemic control. Such GLP1 variants and GLP1 receptor agonists could be used to treat obesity and diabetes.

BRIEF SUMMARY OF THE INVENTION

According to one aspect, the present invention provides glucagon-like peptide 1 (GLP1) variants comprising at least one amino acid modification from mature GLP1 (7-37) (SEQ ID NO: 4) selected from the group consisting of: (i) addition of an amino acid to the N-terminus; and (ii) deletion of an amino acid from the peptide sequence. In certain embodiments, the modification comprises addition of alanine or glutamine to the N-terminus.

According to one aspect, the present invention provides GLP1 receptor agonists, wherein the GLP1 receptor agonists comprise fusion proteins comprising GLP1 or a variant thereof. In certain embodiments, the GLP1 receptor agonists comprise GLP1 peptide or a GLP1 peptide variant fused to a stabilizing domain. In one embodiment, the stabilizing domain is an antibody or antigen-binding fragment thereof that binds to GLP1 receptor.

The GLP1 receptor agonists of the present invention are useful, inter alia, for increasing the binding and/or activity of GLP1. In some embodiments, the GLP1 receptor agonists of the present invention function by activating GLP1 and reducing blood sugar levels. In some embodiments, the GLP1 peptide variants and/or GLP1 receptor agonists of the present invention are more resistant to inactivation by dipeptidyl peptidase 4 (DPP4) and show improved half-life in vivo. The improved GLP1 agonists of the present invention lead to significant reduction in blood sugar levels which is sustained for more than 10 days even with a single dose. In some embodiments, the GLP1 receptor agonists function by potentiating glucose-induced secretion of insulin from pancreatic beta cells, increasing insulin expression, inhibiting beta-cell apoptosis, promoting beta-cell neogenesis, reducing glucagon secretion, delaying gastric emptying, promoting satiety and increasing peripheral glucose disposal. In certain embodiments, the GLP1 receptor agonists are useful in preventing, treating or ameliorating at least one symptom of a hyperglycemia-associated disease or disorder (e.g., diabetes) in a subject. In certain embodiments, the GLP1 receptor agonists may be administered prophylactically or therapeutically to a subject having or at risk of having diabetes. In certain embodiments, the GLP1 receptor agonists are useful in preventing, treating or ameliorating at least one symptom or indication of obesity, such as weight loss, in a subject.

In certain embodiments, the GLP1 receptor agonists are fusion proteins comprising a GLP1 variant and a stabilizing domain, wherein the stabilizing domain comprises an immunoglobulin or fragment thereof. In a specific embodiment, the immunoglobulin comprises a heavy chain variable region and a light chain variable region and specifically binds to GLP1 receptor. In certain embodiments, the GLP1 receptor agonists bind to GLP1 receptor leading to GLP1 receptor activation. In certain embodiments, the GLP1 receptor agonists function by activating GLP1 receptor leading to glycemic control, i.e., reduction of blood glucose levels.

In one embodiment, the invention provides a fusion protein that has one or more of the following characteristics: (a) comprises a GLP1 variant domain and a stabilizing domain; (b) is a GLP1 receptor agonist; (c) the GLP1 variant domain comprises the amino acid sequence of SEQ ID NO: 5, 6, 7 or 8; (d) binds to GLP1 receptor; (e) the stabilizing domain comprises an immunoglobulin or fragment thereof; (f) the stabilizing domain comprises an immunoglobulin Fc fragment; (g) the stabilizing domain comprises an anti-GLP1 receptor antibody or antigen-binding fragment thereof; (h) is resistant to degradation by serum proteases for at least 72 hours; and (i) results in significant reduction in serum glucose level which is sustained for more than 10 days with a single dose of administration.

In one aspect, the present invention provides nucleic acid molecules encoding GLP1 variants or portions thereof. For example, the present invention provides nucleic acid molecules encoding any of the amino acid sequences selected from the group consisting of SEQ ID Nos: 5, 6, 7, 8, 9, 10, 11, 12 and 13, or a substantially similar sequence thereof having at least 90%, at least 95%, at least 98% or at least 99% sequence identity thereto.

The present invention also provides nucleic acid molecules encoding any of the fusion proteins comprising GLP1 variants.

In a related aspect, the present invention provides recombinant expression vectors capable of expressing a polypeptide comprising a GLP1 variant or a fusion protein comprising a GLP1 variant as described herein. For example, the present invention includes recombinant expression vectors comprising any of the nucleic acid molecules mentioned above, i.e., nucleic acid molecules encoding any of the GLP1 variants or fusion proteins comprising GLP1 variants. Also included within the scope of the present invention are host cells into which such vectors have been introduced, as well as methods of producing the proteins or fragments thereof by culturing the host cells under conditions permitting production of the proteins or fragments thereof, and recovering the proteins and fragments so produced.

In one aspect, the invention provides a pharmaceutical composition comprising a therapeutically effective amount of at least one recombinant protein or fragment thereof which specifically binds GLP1 receptor and a pharmaceutically acceptable carrier. In a related aspect, the invention features a composition, which is a combination of a GLP1 receptor agonist protein and a second therapeutic agent. In one embodiment, the second therapeutic agent is any agent that is advantageously combined with a GLP1 receptor agonist. Exemplary agents that may be advantageously combined with a GLP1 receptor agonist include, without limitation, other agents that activate GLP1 receptor activity (including other proteins or metabolites, etc.) and/or agents which do not directly bind GLP1 receptor but nonetheless alleviate or ameliorate or treat a GLP1 receptor-associated disease or disorder (e.g., diabetes). Additional combination therapies and co-formulations involving the GLP1 receptor agonist proteins of the present invention are disclosed elsewhere herein.

In another aspect, the invention provides therapeutic methods for treating a disease or disorder associated with GLP1 such as diabetes in a subject using a GLP1 receptor agonist of the invention, wherein the therapeutic methods comprise administering a therapeutically effective amount of a pharmaceutical composition comprising a GLP1 receptor agonist of the invention to the subject in need thereof. In certain embodiments, the GLP1 receptor agonist comprises a GLP1 variant or fusion protein comprising a GLP1 variant. The disorder treated is any disease or condition which is improved, ameliorated, inhibited or prevented by activation of GLP1 receptor activity. In certain embodiments, the invention provides methods to prevent, treat or ameliorate at least one symptom of a GLP1 receptor-associated disease or disorder, the method comprising administering a therapeutically effective amount of a GLP1 receptor agonist of the invention to a subject in need thereof. In some embodiments, the present invention provides methods to ameliorate or reduce the severity of at least one symptom or indication of GLP1 receptor-associated disease or disorder in a subject by administering a therapeutically effective amount of a GLP1 receptor agonist protein of the invention, wherein the at least one symptom or indication is selected from the group consisting of high blood sugar levels, excessive thirst, increased urination, presence of ketones in urine, fatigue, weight fluctuations, blurred vision, slow healing sores, frequent infections, swollen or tender gums, obesity, heart disease, stroke, kidney disease, eye disease, nerve damage and high blood pressure. In certain embodiments, the invention provides methods to reduce body weight in an overweight or obese subject, the methods comprising administering to the subject a therapeutically effective amount of a GLP1 receptor agonist of the invention that binds GLP1 receptor and activates GLP1 receptor activity. In certain embodiments, the invention provides methods to reduce blood sugar levels in a subject, the methods comprising administering to the subject a therapeutically effective amount of a GLP1 receptor agonist of the invention that binds GLP1 receptor and activates GLP1 receptor activity. In some embodiments, the GLP1 receptor agonist may be administered prophylactically or therapeutically to a subject having or at risk of having hyperglycemia. The subjects at risk include, but are not limited to, subjects of advanced age, pregnant women, subjects with high HbA1c levels, and subjects with one or more risk factors including obesity, high blood cholesterol, smoking, excessive alcohol consumption, and/or lack of exercise. In certain embodiments, the invention provides methods to treat type 2 diabetes that is uncontrolled by treatment with insulin and/or metformin, the methods comprising administering a therapeutically effective amount of a GLP1 receptor agonist of the invention to a subject in need thereof. In certain embodiments, the GLP1 receptor agonist of the invention is administered in combination with a second therapeutic agent to the subject in need thereof. The second therapeutic agent may be selected from the group consisting of an insulin or insulin analogue, a biguanide (e.g., metformin), a thiazolidinedione, a sulfonylurea (e.g., chlorpropamide), a glinide (e.g., nateglinide), an alpha glucosidase inhibitor, a DPP4 inhibitor (e.g., sitagliptin), pramlintide, bromocriptine, a SGLT2 inhibitor (e.g., canagliflozin), an anti-hypertensive drug, a statin, aspirin, dietary modification, exercise, and a dietary supplement. Additional therapeutic agents that can be used in combination with the GLP1 receptor agonist fusion proteins of the present invention are described elsewhere herein. In certain embodiments, the second therapeutic agent may be an agent that helps to counteract or reduce any possible side effect(s) associated with a GLP1 receptor agonist of the invention, if such side effect(s) should occur. The GLP1 receptor agonist may be administered subcutaneously, intravenously, intradermally, intraperitoneally, orally, intramuscularly, or intracranially. The GLP1 receptor agonist may be administered at a dose of about 0.1 mg/kg of body weight to about 100 mg/kg of body weight of the subject. In certain embodiments, a GLP1 receptor agonist of the present invention may be administered at one or more doses comprising between 0.1 mg to 600 mg.

The present invention also includes use of a GLP1 receptor agonist of the invention in the manufacture of a medicament for the treatment of a disease or disorder that would benefit from the stimulation of GLP1 receptor binding and/or activity (e.g., diabetes including type 2 diabetes).

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "GLP1", also called as "glucagon-like peptide 1", refers to the 31-amino acid peptide hormone released from intestinal L cells following nutrient consumption. GLP1 binds to GLP1 receptor and potentiates the glucose-induced secretion of insulin from pancreatic beta cells, increases insulin expression, inhibits beta-cell apoptosis, promotes beta-cell neogenesis, reduces glucagon secretion, delays gastric emptying, promotes satiety and increases peripheral glucose disposal. In certain embodiments, the term "GLP1" refers to the mature 31 amino acid peptide hormone (SEQ ID NO: 4) comprising amino acids 7 to 37 of full length GLP1 peptide (SEQ ID NO: 3). The term also includes variants of GLP1 wherein the variants comprise 1, 2, 3, 4, 5 or 6 amino acid substitutions, additions or deletions. For example, the term includes variants that comprise amino acid sequences of SEQ ID NOs: 5, 6, 7, or 8.

As used herein, a "stabilizing domain" is any macromolecule that when fused to a peptide increases the in vivo activity and/or stability of the peptide. For example, a stabilizing domain may be a polypeptide comprising an immunoglobulin $C_H3$ domain. In certain embodiments, the stabilizing domain increases the serum half-life of the peptide. In certain embodiments, the stabilizing peptide increases the in vivo potency of the peptide. A non-limiting example of a stabilizing domain is an Fc portion of an immunoglobulin, e.g., an Fc domain of an IgG selected from the isotypes IgG1, IgG2, IgG3, and IgG4, as well as any allotype within each isotype group. In certain embodiments, the stabilizing domain is an Fc fragment or an amino acid sequence of 1 to about 200 amino acids in length containing at least one cysteine residues. As another example, a stabilizing domain may be an immunoglobulin or an antigen-binding fragment thereof. In certain embodiments, the stabilizing domain is an immunoglobulin comprising a heavy chain variable region and a light chain variable region wherein the immunoglobulin binds to a specific antigen. In certain embodiments, the stabilizing domain comprises an antigen-binding domain and a Fc domain (for example, of an IgG1 or IgG4 antibody) or may comprise only an antigen-binding portion (for example, a Fab, F(ab')$_2$ or scFv fragment), and may be modified to affect functionality. In a specific embodiment, the stabilizing domain is an immunoglobulin comprising a heavy chain variable region and a light chain variable region wherein the immunoglobulin binds to GLP1 receptor. In other embodiments, the stabilizing domain is a cysteine residue or a short cysteine-containing peptide. Other stabilizing domains include peptides or polypeptides comprising or consisting of a leucine zipper, a helix-loop motif, or a coiled-coil motif.

As used herein, the term "GLP1 receptor agonist" refers to a protein that binds to GLP1 receptor. In the context of the present invention, the term refers to a fusion protein comprising GLP1 or a GLP1 variant fused to a stabilizing domain. In certain embodiments, the term includes fusion proteins comprising a GLP1 variant fused to an immunoglobulin or fragment thereof. In specific embodiments, the term includes fusion proteins comprising GLP1 or a GLP1 variant fused to the N-terminal of light chain variable region (VL) of an immunoglobulin. In one specific embodiment, the term includes GLP1 or a GLP1 variant fused to the N-terminal of VL of an antibody or antigen-binding fragment thereof that binds to GLP1 receptor.

The term "antibody", as used herein, is intended to refer to immunoglobulin molecules comprised of four polypeptide chains, two heavy (H) chains and two light (L) chains inter-connected by disulfide bonds, as well as multimers thereof (e.g. IgM) or antigen-binding fragments thereof. Each heavy chain is comprised of a heavy chain constant region (comprised of domains $C_H1$, $C_H2$ and $C_H3$) and an Ig variable region which may be a heavy chain variable region ("HCVR" or "$V_H$") or a light chain variable region ("LCVR or "$V_L$"). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs. The term "antigen-binding protein", as used herein, also includes antibodies.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

Methods and techniques for identifying CDRs within VR amino acid sequences are well known in the art and can be used to identify CDRs within the specified VR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within the antigen-binding domain of an antigen-binding protein or an antibody.

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The terms "antigen-binding portion" of an antigen-binding protein, "antigen-binding fragment" of an antigen-binding protein, and the like, as used herein, include any naturally occurring, enzymatically obtainable, synthetic, or genetically engineered polypeptide or glycoprotein that specifically binds an antigen to form a complex. The terms "antigen-binding fragment" of an antigen-binding protein, or "antigen-binding protein fragment", as used herein, refers to one or more fragments of an antigen-binding protein that retain the ability to specifically bind to GLP1 receptor. An antigen-binding protein fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antigen-binding protein or an antibody may be derived, e.g., from full protein molecules using any suitable standard techniques such as proteolytic digestion or recombinant genetic engineering techniques involving the manipulation and expression of DNA encoding antigen-binding protein variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antigen-binding protein or an antibody of the present invention will typically comprise at least one immunoglobulin (Ig) variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antigen-binding protein may contain a monomeric $V_H$ or $V_L$ domain.

In certain embodiments, an antigen-binding fragment may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3, (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antigen-binding protein of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full protein molecules, antigen-binding fragments may be mono-specific or multi-specific (e.g., bi-specific). A multi-specific antigen-binding fragment of an antigen-binding protein will typically comprise at least two different variable domains, wherein each variable domain is capable of specifically binding to a separate antigen or to a different epitope on the same antigen. Any multi-specific antigen-binding protein format, including the exemplary bi-specific antigen-binding protein formats disclosed herein, may be adapted for use in the context of an antigen-binding fragment of an antigen-binding protein of the present invention using routine techniques available in the art.

The terms "fully human antibody", "human antibody", "fully human antigen-binding protein", or "human antigen-binding protein", as used herein, are intended to include antigen-binding proteins having variable and constant regions derived from human germline immunoglobulin sequences. The human antigen-binding proteins of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antigen-binding protein", as used herein, is not intended to include antigen-binding proteins in which CDR sequences derived from the germline of another mammalian species (e.g., mouse), have been grafted onto human FR sequences. The term includes antigen-binding proteins or antibodies recombinantly produced in a non-human mammal, or in cells of a non-human mammal. The term is not intended to include antigen-binding proteins or antibodies isolated from or generated in a human subject.

The term "recombinant", as used herein, refers to fusion proteins or fragments thereof of the invention created, expressed, isolated or obtained by technologies or methods known in the art as recombinant DNA technology which include, e.g., DNA splicing and transgenic expression. The term refers to fusion proteins expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, isothermal titration calorimetry, and the like.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antigen-binding protein or antibody, or "antibody fragment", as used herein, refers to one or more fragments of an immunoglobulin protein that retain the ability to bind to GLP1 receptor.

The term "$K_D$", as used herein, is intended to refer to the equilibrium dissociation constant of a particular protein-antigen interaction.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder associated with GLP1. The term includes human subjects who have or are at risk of having a disease or disorder associated with GLP1. For example, the term includes subjects that have or are at risk for developing diabetes (e.g., Type 2 diabetes). In certain embodiments, the term includes subjects that have or are at risk for developing obesity, stroke or myocardial infarction. The term also includes subjects that have high blood sugar levels, and/or increased levels of one or more bio markers for diabetes, e.g., HbA1c. The term also includes subjects with diabetes for whom a standard-of-care therapy (e.g., metformin) is contraindicated or not tolerated or whose disease in uncontrolled despite treatment (e.g., with metformin).

As used herein, the terms "treat", "treating", or "treatment" refer to the reduction or amelioration of the severity of at least one symptom or indication of a disease or disorder associated with GLP1 due to the administration of a therapeutic agent such as a GLP1 receptor agonist of the present invention to a subject in need thereof. The terms include inhibition of progression of disease or of worsening of symptoms. The terms also include positive prognosis of disease, i.e., the subject may be free of a symptom or indication or may have reduced intensity of a symptom or indication upon administration of a therapeutic agent such as a GLP1 receptor agonist protein of the present invention. For example, a subject with diabetes may have reduction in blood glucose levels upon administration of a GLP1 receptor agonist of the invention. The therapeutic agent may be administered at a therapeutic dose to the subject.

The terms "prevent", "preventing" or "prevention" refer to inhibition of manifestation of any symptoms or indications of a disease or disorder associated with hyperglycemia upon administration of a GLP1 receptor agonist of the present invention. The term includes inhibition of manifestation of a symptom or indication of a GLP1 receptor-associated disease or disorder in a subject at risk for developing such a disease or disorder.

GLP1 (7-37) (SEQ ID NO: 4) has a very short half-life of in circulation (1-2 minutes), due to its rapid inactivation by the enzyme dipeptidyl peptidase 4 (DPP4). Previous work has shown that various amino acid substitutions at position 8 of GLP1 (7-37) make it more resistant to DPP4, thus conferring a longer half-life. However, there is residual susceptibility of these molecules to DPP4 cleavage (Deacon et al 1998, Diabetologia 41: 271-278). Thus, there is a need to develop new molecules that have increased resistance to degradation by DPP4.

The present inventors hypothesized that to confer better resistance to DPP4, a first step was to introduce mutations that lengthen or shorten the amino terminus of GLP1 by either addition of an amino acid (i.e., Ala, Gln) to the N-terminus or deletion of His or Ala within the peptide sequence to provide better resistance to DPP4 cleavage. The present inventors have shown herein that these novel GLP1 variants are indeed highly resistant to degradation by DPP4. A second step was to compensate for any weakened or reduced GLP1 activity by fusing the GLP1 to an anti-GLP1 receptor antibody, which tethers the weakened GLP1 to the GLP1 receptor and thereby increases its potency. Further, the present inventors found that these fusion proteins, likely because they contain an Fc domain, had an increased serum half-life and led to increased reduction of blood sugar levels that was sustained for more than 10 days. The novel GLP1 variants and fusion proteins disclosed herein have significantly improved resistance to degradation by DPP4 in vitro and in vivo and show vastly improved potency in glycemic control as shown herein. The terms "significantly improved" or "enhanced" or "increased", as used herein, in the context of resistance to degradation by DPP4 refer to increased resistance to degradation upon incubation with DPP4 for more than 4 hours, more than 8 hours, more than 16 hours, more than 24 hours, more than 36 hours or more than 70 hours, as measured by the assays described herein. The terms "significantly improved" or "enhanced" or "increased", as used herein, in the context of reduction of blood sugar levels refers to sustained lowering of blood sugar levels for more than 1 day, more than 2 days, more than 3 days, more than 4 days, more than 5 days, more than 6 days, more than 7 days, more than 8 days, more than 9 days, or more than 10 days in a subject upon administration of a GLP1 receptor agonist of the present invention.

The GLP1 receptor agonists of the present invention bind to GLP1 receptor with high affinity and lead to GLP1 receptor activation. In some embodiments, the proteins are useful for treating a subject suffering from diabetes. The proteins when administered to a subject in need thereof may reduce blood sugar levels in the subject. They may be used alone or as adjunct therapy with other therapeutic moieties or modalities known in the art for treating hyperglycemia.

Certain GLP1 receptor agonist proteins of the present invention are able to bind to and stimulate the activity of GLP1 receptor, as determined by in vitro or in vivo assays. The ability of the proteins of the invention to bind to and enhance the activity of GLP1 receptor may be measured using any standard method known to those skilled in the art, including binding assays, or activity assays, as described herein.

The antigen-binding proteins specific for GLP1 receptor may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antigen-binding proteins may be used in diagnostic assays including imaging assays.

Bioequivalents

The GLP1 receptor agonists of the present invention encompass proteins having amino acid sequences that vary from those of the described GLP1 receptor agonists, but that retain the ability to bind GLP1 receptor. Such variant GLP1 receptor agonists comprise one or more additions, deletions, or substitutions of amino acids when compared to parent sequence, but exhibit biological activity that is essentially equivalent to that of the described GLP1 receptor agonists. Likewise, the GLP1 receptor agonist-encoding DNA sequences of the present invention encompass sequences that comprise one or more additions, deletions, or substitutions of nucleotides when compared to the disclosed sequence, but that encode a GLP1 receptor agonist that is essentially bioequivalent to a GLP1 receptor agonist of the invention.

Two proteins are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two GLP1 receptor agonist proteins are bioequivalent if there are no clinically meaningful differences in their safety, purity, or potency.

In one embodiment, two GLP1 receptor agonist proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two GLP1 receptor agonist proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the protein (or its target) is measured as a function of time; and (d) in a well-controlled clinical trial that establishes safety, efficacy, or bioavailability or bioequivalence of an antigen-binding protein.

Bioequivalent variants of the GLP1 receptor agonist proteins of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent proteins may include variants comprising amino acid changes, which modify the glycosylation characteristics of the proteins, e.g., mutations that eliminate or remove glycosylation.

Biological Characteristics of the GLP1 Receptor Agonists

In general, the GLP1 receptor agonists of the present invention function by binding to GLP1 receptor and facilitate activation of GLP1 receptor upon binding. In certain embodiments, the proteins of the present invention bind with high affinity to GLP1 receptor. For example, the present invention includes GLP1 receptor agonists that that lead to activation of the GLP1 receptor (e.g., at 25° C. or at 37° C.) as measured by luciferase assay, e.g., using the assay format as defined in Example 2 herein. In certain embodiments, the GLP1 receptor agonists activate GLP1 receptor with a EC50 of less than 10 nM, less than 500 pM, or less than 250 pM, as measured by luciferase assay, e.g., using the assay format as defined in Example 2 herein, or a substantially similar assay.

The present invention also includes GLP1 receptor agonists that reduce blood sugar levels in vivo upon administration to a subject in need thereof, e.g., as shown in Example 3, or a substantially similar assay. The GLP1 receptor agonists affect enhanced glycemic control upon administration, leading to reduction in blood glucose levels. In certain embodiments, even a single therapeutically effective dose of the GLP1 receptor agonists of the present invention leads to significant blood sugar reduction, which is sustained for more than 10 days.

The present invention also includes GLP1 receptor agonists that show enhanced resistance to degradation by serum proteases/peptidases, as measured by mass spectroscopy, e.g., as shown in Example 4 herein, or a substantially similar method. In certain embodiments, the GLP1 receptor agonists are resistant to degradation by dipeptidyl peptidase 4 (DPP4) for more than 4 hours, more than 6 hours, more than 12 hours, more than 24 hours, more than 48 hours, or more than 70 hours, as measured by the assay described in Example 4 herein.

The GLP1 receptor agonists of the present invention may possess one or more of the aforementioned biological characteristics, or any combinations thereof. Other biological characteristics of the proteins of the present invention will be evident to a person of ordinary skill in the art from a review of the present disclosure including the working Examples herein.

Therapeutic Administration and Formulations

The invention provides therapeutic compositions comprising the GLP1 receptor agonists of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of GLP1 receptor agonist may vary depending upon the age and the size of a subject to be administered, target disease, conditions, route of administration, and the like. When an antigen-binding protein of the present invention is used for treating a disease or disorder in an adult patient, or for preventing such a disease, it is advantageous to administer the antigen-binding protein of the present invention normally at a single dose of about 0.001 to about 100 mg/kg body weight, more preferably about 0.001 to about 60, about 0.01 to about 10, or about 0.01 to about 1 mg/kg body weight. Depending on the severity of the condition, the frequency and the duration of the treatment can be adjusted. In certain embodiments, the antigen-binding protein or antigen-binding fragment thereof of the invention can be administered as an initial dose of at least about 0.001 mg to about 100 mg, about 0.001 to about 50 mg, about 0.005 to about 50 mg, about 0.01 to about 40 mg, to about 30 mg, or to about 10 mg. In certain embodiments, the initial dose may be followed by administration of a second or a plurality of subsequent doses of the GLP1 receptor agonist in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the GLP1 receptor agonists of the present invention is also contemplated herein. Protein-conjugated nanoparticles may be used both for therapeutic and diagnostic applications. Nanoparticles may be developed and conjugated to antigen-binding proteins contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™ OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the GLP1 receptor agonist contained is generally about 0.001 to about 100 mg per dosage form in a unit dose; especially in the form of injection, it is preferred that the GLP1 receptor agonist is contained in about 0.001 to about 100 mg and in about 0.01 to about 100 mg for the other dosage forms.

Therapeutic Uses of the GLP1 Receptor Agonists

The GLP1 receptor agonists of the present invention are useful for the treatment, and/or prevention of a disease or disorder or condition associated with hyperglycemia such as diabetes and/or for ameliorating at least one symptom associated with such disease, disorder or condition. In one embodiment, a GLP1 receptor agonist of the invention may be administered at a therapeutic dose to a patient with diabetes (e.g., type 2 diabetes).

In certain embodiments, the GLP1 receptor agonists of the invention are useful to treat subjects suffering from a disease or disorder selected from the group consisting of diabetes mellitus, obesity, insulin resistance, hypertension, dyslipidemia, Type 2 diabetes, Type 1 diabetes, pre-diabetes, cardiovascular disease, atherosclerosis, congestive heart failure, coronary heart disease, arteriosclerosis, peripheral artery disease, stroke, respiratory dysfunction, renal disease, fatty liver disease, non-alcoholic steatohepatitis (NASH), and metabolic syndrome.

In certain embodiments, the GLP1 receptor agonists of the invention are useful to treat subjects that are overweight or obese and/or prevent or treat one or more obesity-associated disorders such as heart disease, stroke, and diabetes.

In certain embodiments, the GLP1 receptor agonists of the invention are useful to treat subjects suffering from diabetes and/or prevent one or more complications of diabetes such as heart disease, stroke, kidney disease, retinopathy, blindness and nerve damage.

It is also contemplated herein to use one or more GLP1 receptor agonist proteins of the present invention prophylactically to subjects at risk for developing diabetes (e.g., type 2 diabetes). The subjects at risk include, but are not limited to, subjects of advanced age, pregnant women, and subjects with one or more risk factors including family history of obesity, high blood cholesterol, smoking, excessive alcohol consumption, and/or lack of exercise.

In a further embodiment, the proteins of the invention are used for the preparation of a pharmaceutical composition or medicament for treating patients suffering from a disease or disorder such as diabetes and obesity. In another embodiment of the invention, the present GLP1 receptor agonists are used as adjunct therapy with any other agent or any other therapy known to those skilled in the art useful for treating or ameliorating a disease or disorder associated with hyperglycemia such as diabetes (e.g., type 2 diabetes).

Combination Therapies

Combination therapies may include a GLP1 receptor agonist of the invention and any additional therapeutic agent that may be advantageously combined with the GLP1 receptor agonist of the invention, or with a biologically active fragment thereof of the invention. The GLP1 receptor agonists of the present invention may be combined synergistically with one or more drugs or therapy used to treat any disease or disorder associated with hyperglycemia (e.g., diabetes). In some embodiments, the GLP1 receptor agonists of the invention may be combined with a second therapeutic agent to reduce blood sugar levels in a subject, or to ameliorate one or more symptoms of diabetes.

The GLP1 receptor agonists of the present invention may be used in combination with an insulin (insulin or an insulin analog), insulin sensitizers such as biguanides (e.g., metformin), and thiazolidinediones (e.g., rosiglitazone), insulin secretagogues such as sulphonylureas (e.g., chlorpropamide), and glinides (e.g., nateglinide), alpha-glucosidase inhibitors (e.g., acarbose), dipeptidyl peptidase 4 (DPP4) inhibitors (e.g., sitagliptin), pramlinitide, bromocriptine, sodium glucose cotransporter 2 (SGLT-2) inhibitors (e.g., canagliflozin), an anti-hypertensive drug (e.g., an angiotensin-converting enzyme inhibitor, an angiotensin receptor blocker, a diuretic, a calcium channel blocker, an alpha-adrenoceptor blocker, an endothelin-1 receptor blocker, an organic nitrate, and a protein kinase C inhibitor), a statin, aspirin, a different GLP1 receptor agonist, a dietary supplement or any other therapy (e.g., exercise) to treat or manage diabetes. In certain embodiments, the GLP1 receptor agonists of the present invention may be administered in combination with a second therapeutic agent or therapy selected from the group consisting of insulin, an insulin analog, metformin, rosiglitazone, pioglitazone, chlorpropamide, glibenclamide, glimepiride, glipizide, tolazamide, tolbutamide, nateglinide, repaglinide, acarbose, miglitol, exenatide, liraglutide, albiglutide, dulaglutide, sitagliptin, saxagliptin, linagliptin, alogliptin, pramlinitide, bromocriptine quick-release, canagliflozin, dapagliflozin, empagliflozin, diet modifications and exercise.

As used herein, the term "in combination with" means that additional therapeutically active component(s) may be administered prior to, concurrent with, or after the administration of the GLP1 receptor agonist of the present invention. The term "in combination with" also includes sequential or concomitant administration of a GLP1 receptor agonist and a second therapeutic agent.

The additional therapeutically active component(s) may be administered to a subject prior to administration of a GLP1 receptor agonist of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of a GLP1 receptor agonist of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of a GLP1 receptor agonist of the present invention. "Concurrent" administration, for purposes of the present invention, includes, e.g., administration of a GLP1 receptor agonist and an additional therapeutically active component to a subject in a single dosage form, or in separate dosage forms administered to the subject within about 30 minutes or less of each other. If administered in separate dosage forms, each dosage form may be administered via the same route (e.g., both the GLP1 receptor agonist and the additional therapeutically active component may be administered intravenously, etc.); alternatively, each dosage form may be administered via a different route (e.g., the GLP1 receptor agonist may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of a GLP1 receptor agonist "prior to", "concurrent with," or "after" (as those terms are defined herein above) administration of an additional therapeutically active component is considered administration of a GLP1 receptor agonist "in combination with" an additional therapeutically active component.

The present invention includes pharmaceutical compositions in which a GLP1 receptor agonist of the present invention is co-formulated with one or more of the additional therapeutically active component(s) as described elsewhere herein.

Administration Regimens

According to certain embodiments, a single dose of a GLP1 receptor agonist of the invention (or a pharmaceutical composition comprising a combination of a GLP1 receptor agonist and any of the additional therapeutically active agents mentioned herein) may be administered to a subject in need thereof. According to certain embodiments of the present invention, multiple doses of a GLP1 receptor agonist (or a pharmaceutical composition comprising a combination of a GLP1 receptor agonist and any of the additional therapeutically active agents mentioned herein) may be administered to a subject over a defined time course. The methods according to this aspect of the invention comprise sequentially administering to a subject multiple doses of a GLP1 receptor agonist of the invention. As used herein, "sequentially administering" means that each dose of GLP1 receptor agonist is administered to the subject at a different point in time, e.g., on different days separated by a predetermined interval (e.g., hours, days, weeks or months). The present invention includes methods which comprise sequentially administering to the patient a single initial dose of a GLP1 receptor agonist, followed by one or more secondary doses of the GLP1 receptor agonist, and optionally followed by one or more tertiary doses of the GLP1 receptor agonist.

The terms "initial dose," "secondary doses," and "tertiary doses," refer to the temporal sequence of administration of the GLP1 receptor agonist of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of GLP1 receptor agonist, but generally may differ from one another in terms of frequency of administration. In certain embodiments, however, the amount of GLP1 receptor agonist contained in the initial, secondary and/or tertiary doses varies from one another (e.g., adjusted up or down as appropriate) during the course of treatment. In certain embodiments, one or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1%, 2, 2%, 3, 3%, 4, 4%, 5, 5%, 6, 6%, 7, 7%, 8, 8%, 9, 9%, 10, 10%, 11, 11%, 12, 12%, 13, 13%, 14, 14%, 15, 15%, 16, 16%, 17, 17%, 18, 18%, 19, 19%, 20, 20%, 21, 21%, 22, 22%, 23, 23%, 24, 24%, 25, 25%, 26, 26%, or more) after the immediately preceding dose. The phrase "the immediately preceding dose," as used herein, means, in a sequence of multiple administrations, the dose of the GLP1 receptor agonist which is administered to a patient prior to the administration of the very next dose in the sequence with no intervening doses. In certain embodiments, each secondary and/or tertiary dose is administered every day, every 2 days, 3 days, 4 days, 5 days, 6 days, or 7 days after the immediately preceding dose. In certain embodiments, each secondary and/or tertiary dose is administered every 0.5 weeks, 1 week, 2 weeks, 3 weeks, or 4 weeks after the immediately preceding dose.

The methods according to this aspect of the invention may comprise administering to a patient any number of secondary and/or tertiary doses of a GLP1 receptor agonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Dosage

The amount of GLP1 receptor agonist administered to a subject according to the methods of the present invention is, generally, a therapeutically effective amount. As used herein, the phrase "therapeutically effective amount" means an amount of GLP1 receptor agonist that results in one or more of: (a) reduction of high sugar levels to normal levels (e.g., pre-prandial blood glucose levels of 80-130 mg/dL; and/or (b) a detectable improvement in one or more symptoms or indicia of diabetes.

In the case of a GLP1 receptor agonist, a therapeutically effective amount can be from about 0.001 mg to about 100 mg, e.g., about 0.001 mg, about 0.002 mg, about 0.003 mg, about 0.004 mg, about 0.005 mg, about 0.006 mg, about 0.007 mg, about 0.008 mg, about 0.009 mg, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg of the GLP1 receptor agonist. In certain embodiments, 0.005 mg to 50 mg, 0.005 mg to 30 mg, 0.005 mg to 10 mg, 0.1 mg to 10 mg, or 0.1 mg to 5 mg of a GLP1 receptor agonist is administered to a subject in need thereof.

The amount of GLP1 receptor agonist contained within the individual doses may be expressed in terms of milligrams of antibody per kilogram of subject body weight (i.e., mg/kg). For example, the GLP1 receptor agonist may be administered to a subject at a dose of about 0.0001 to about 100 mg/kg of subject body weight.

Selected Embodiments

In Embodiment, 1, the present invention provides a glucagon-like peptide 1 (GLP1) variant comprising mature GLP1 (7-37) (SEQ ID NO: 4) having at least one amino acid modification selected from the group consisting of: (i) addition of an amino acid to the N-terminus; and (ii) deletion of an amino acid from the peptide sequence; wherein the GLP1 variant has enhanced resistance to proteolytic cleavage and/or enhanced blood glucose lowering ability.

In Embodiment, 2, the present invention provides the GLP1 variant of embodiment 1, wherein the amino acid modification comprises addition of an amino acid selected from the group consisting of alanine (Ala) and glutamine (Gln) to the N-terminus.

In Embodiment 3, the present invention provides the GLP1 variant of embodiment 1 or 2, wherein the amino acid modification comprises addition of Gln to the N-terminus.

In Embodiment 4, the present invention provides the GLP1 variant of embodiment 1, wherein the amino acid modification comprises deletion of histidine (His1) or alanine (Ala2) from SEQ ID NO: 4.

In Embodiment 5, the present invention provides the GLP1 variant of any one of embodiment 1-4 comprising an amino acid sequence selected from the group consisting of SEQ ID NOs: 5, 6, 7 and 8.

In Embodiment 6, the present invention provides the GLP1 variant of embodiment 5 comprising an amino acid sequence of SEQ ID NO: 6.

In Embodiment 7, the present invention provides a fusion protein comprising the GLP1 variant of any one of embodiments 1-6 fused to a stabilizing domain, wherein the stabilizing domain is an antigen-binding protein or antigen-binding fragment thereof that specifically binds GLP1 receptor and that comprises a heavy chain variable region (HCVR) and a light chain variable region (LCVR).

In Embodiment 8, the present invention provides the fusion protein of embodiment 7, wherein the GLP1 variant is fused to the N-terminal or C-terminal of the HCVR of the antigen-binding protein or antigen-binding fragment thereof.

In Embodiment 9, the present invention provides the fusion protein of embodiment 7, wherein the GLP1 variant is fused to the N-terminal or C-terminal of the LCVR of the antigen-binding protein or antigen-binding fragment thereof.

In Embodiment 10, the present invention provides a fusion protein comprising a GLP1 variant of any one of embodiments 1-6 fused to a stabilizing domain, wherein the stabilizing domain is an immunoglobulin (Ig) or fragment thereof.

In Embodiment 11, the present invention provides the fusion protein of embodiment 11 comprising an amino acid sequence selected from the group consisting of SEQ ID Nos: 9, 10, 11, 12 and 13.

In Embodiment 12, the present invention provides a fusion protein comprising a GLP1 variant fused to a stabilizing domain, wherein the stabilizing domain is an antigen-binding protein or antigen-binding fragment thereof, wherein the antigen-binding protein or fragment thereof comprises a heavy chain variable region (HCVR) and a light chain variable region (LCVR).

In Embodiment 13, the present invention provides the fusion protein of embodiment 12, wherein the GLP1 variant is fused to N-terminal or C-terminal of the HCVR of the antigen-binding protein or fragment thereof.

In Embodiment 14, the present invention provides the fusion protein of embodiment 12, wherein the GLP1 variant is fused to N-terminal or C-terminal of the LCVR of the antigen-binding protein or fragment thereof.

In Embodiment 15, the present invention provides the fusion protein of any one of embodiments 12-14, wherein the antigen-binding protein or fragment thereof binds specifically to GLP1 receptor.

In Embodiment 16, the present invention provides the fusion protein of any one of embodiments 12-15 comprising the GLP1 variant of any of the above embodiments.

In Embodiment 17, the present invention provides the fusion protein of any one of embodiments 12-16, wherein the GLP1 variant comprises an amino acid sequence selected from the group consisting of SEQ ID NOs: 5, 6, 7 and 8.

In Embodiment 18, the present invention provides the fusion protein of embodiment 16 or 17, wherein the GLP1 variant comprises an amino acid sequence of SEQ ID NO: 6.

In Embodiment 19, the present invention provides a GLP1 receptor agonist comprising a GLP1 variant wherein the GLP1 variant is fused to a stabilizing domain, wherein the stabilizing domain is an antigen-binding protein or antigen-binding fragment thereof, wherein the antigen-binding protein or fragment thereof comprises a heavy chain variable region (HCVR) and a light chain variable region (LCVR).

In Embodiment 20, the present invention provides the GLP1 receptor agonist of embodiment 19, wherein the GLP1 variant is fused to N-terminal or C-terminal of the HCVR of the antigen-binding protein or fragment thereof.

In Embodiment 21, the present invention provides the GLP1 receptor agonist of embodiment 19, wherein the GLP1 variant is fused to N-terminal or C-terminal of the LCVR of the antigen-binding protein or fragment thereof.

In Embodiment 22, the present invention provides the GLP1 receptor agonist of any one of embodiments 19-21, wherein the antigen-binding protein or fragment thereof binds specifically to GLP1 receptor.

In Embodiment 23, the present invention provides the GLP1 receptor agonist of any one of embodiments 19-22 comprising the GLP1 variant of embodiment 1.

In Embodiment 24, the present invention provides the GLP1 receptor agonist of any one of embodiments 19-23, wherein the GLP1 variant comprises an amino acid sequence selected from the group consisting of SEQ ID NOs: 5, 6, 7 and 8.

In Embodiment 25, the present invention provides the GLP1 receptor agonist of embodiment 23 or 24, wherein the GLP1 variant comprises an amino acid sequence of SEQ ID NO: 6.

In Embodiment 26, the present invention provides a GLP1 receptor agonist comprising a GLP1 variant wherein the GLP1 variant is fused to a stabilizing domain, wherein the stabilizing domain is an immunoglobulin (Ig) or fragment thereof.

In Embodiment 27, the present invention provides the GLP1 receptor agonist of embodiment 26 comprising an amino acid sequence selected from the group consisting of SEQ ID Nos: 9, 10, 11, 12 and 13.

In Embodiment 28, the present invention provides a pharmaceutical composition comprising a protein of any one of embodiments 1-27 and a pharmaceutically acceptable carrier or diluent.

In Embodiment 29, the present invention provides an isolated polynucleotide molecule comprising a polynucleotide sequence that encodes a GLP1 variant as set forth in any one of embodiments 1-6.

In Embodiment 30, the present invention provides an isolated polynucleotide molecule comprising a polynucleotide sequence that encodes a fusion protein as set forth in any one of embodiments 10-11.

In Embodiment 31, the present invention provides an isolated polynucleotide molecule comprising a polynucleotide sequence that encodes a GLP1 receptor agonist as set forth in any one of embodiments 26-27.

In Embodiment 32, the present invention provides a vector comprising the polynucleotide sequence of any one of embodiments 29-31.

In Embodiment 33, the present invention provides a cell expressing the vector of embodiment 32.

In Embodiment 34, the present invention provides a method of lowering blood sugar level comprising administering a pharmaceutical composition comprising a therapeutically effective amount of the protein of any one of embodiments 1-27 to a subject in need thereof.

In Embodiment 35, the present invention provides the method of embodiment 34, wherein the subject has a disease or disorder selected from the group consisting of diabetes mellitus, obesity, insulin resistance, hypertension, dyslipidemia, Type 2 diabetes, Type 1 diabetes, pre-diabetes, cardiovascular disease, atherosclerosis, congestive heart failure, coronary heart disease, arteriosclerosis, peripheral artery disease, stroke, respiratory dysfunction, renal disease, fatty liver disease, non-alcoholic steatohepatitis (NASH), and metabolic syndrome.

In Embodiment 36, the present invention provides a method of preventing, treating or ameliorating at least one symptom, indication or complication of Type 2 diabetes, the method comprising administering a pharmaceutical composition comprising a therapeutically effective amount of the protein of any one of embodiments 1-27 to a subject in need thereof.

In Embodiment 37, the present invention provides the method of embodiment 36, wherein the at least one symptom, indication or complication is selected from the group consisting of high blood sugar levels, excessive thirst, increased urination, presence of ketones in urine, fatigue, weight fluctuations, blurred vision, slow healing sores, frequent infections, swollen or tender gums, obesity, heart disease, stroke, kidney disease, eye disease, nerve damage and high blood pressure.

In Embodiment 38, the present invention provides the method of any one of embodiments 34-37, wherein the pharmaceutical composition is administered in combination with a second therapeutic agent or therapy.

In Embodiment 39, the present invention provides the method of embodiment 38, wherein the second therapeutic agent or therapy is selected from the group consisting of an insulin or insulin analogue, a biguanide (e.g., metformin), a thiazolidinedione, a sulfonylurea (e.g., chlorpropamide), a glinide (e.g., nateglinide), an alpha glucosidase inhibitor, a DPP4 inhibitor (e.g., sitagliptin), pramlintide, bromocriptine, a SGLT2 inhibitor (e.g., canagliflozin), an anti-hypertensive drug, a statin, aspirin, dietary modification, exercise, and a dietary supplement.

In Embodiment 40, the present invention provides the method of any one of embodiments 34-39, wherein the pharmaceutical composition is administered subcutaneously, intravenously, intradermally, intraperitoneally, orally, or intramuscularly.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Exemplary Fusion Proteins Comprising GLP1

GLP1 (7-37) has a very short half-life of in circulation (1-2 minutes), due to its rapid inactivation by the enzyme dipeptidyl peptidase 4 (DPP4). Previous work has shown that various amino acid substitutions at position 8 of GLP1 (7-37) make it more resistant to DPP4, thus conferring a longer half-life (Deacon et al 1998, Diabetologia 41: 271-278). However, there is residual susceptibility of these molecules to DPP4 cleavage. Thus there is a need to develop new molecules that are still more resistant to DPP4.

To confer better resistance to DPP4, a first part of the technology is to introduce mutations that lengthen or shorten the amino terminus of GLP1 by either addition of an amino acid (i.e., Ala, Gln) to the N-terminus or deletion of His7 or Ala8 within the peptide sequence to provide better resistance to DPP4 cleavage. These modifications also weaken the GLP1 activity, and a second part of the technology is to compensate for the reduced activity by tethering the weakened agonist to the receptor using an anti GLP1R antibody by fusing the peptide to the N-terminus of the anti-GLP1R antibody light chain sequence. As proof of concept, modified GLP1 (7-37) ligand sequences were fused to the N-terminus of the light chain of a GLP1R antibody, as described below.

Mature GLP1 is a 31-amino acid peptide hormone comprising amino acids 7 to 37 of full-length GLP1 (SEQ ID NO: 3) and has the amino acid sequence HAEGTFTSDVS-SYLEGQAAKEFIAWLVKGRG (SEQ ID NO: 4).

Mature GLP1 was modified by amino acid deletions or additions at the amino terminus to generate GLP1 variants. Exemplary GLP1 variants are given below:

Des-Ala-GLP1 comprising the amino acid sequence HEGTFTSDVSSYLEGQAAKEFIAWLVKGRG (SEQ ID NO: 5)

Q-GLP1 comprising the amino acid sequence QHAE-GTFTSDVSSYLEGQAAKEFIAWLVKGRG (SEQ ID NO: 6)

A-GLP1 comprising the amino acid sequence AHAE-GTFTSDVSSYLEGQAAKEFIAWLVKGRG (SEQ ID NO: 7)

desH-GLP1 comprising the sequence AEGTFTSDVS-SYLEGQAAKEFIAWLVKGRG (SEQ ID NO: 8)

To compensate for possible reduced activity of the above GLP1 variants, they were tethered to the GLP1 receptor (GLP1R) using an anti-GLP1R antibody or to an antibody Fc fragment. Exemplary fusion proteins comprising mature GLP1 or a GLP1 variant were generated by fusing mature GLP1 or the GLP1 variant to the N-terminal of the light chain of an anti-GLP1 receptor antibody comprising heavy chain variable region of SEQ ID NO: 1 and light chain variable region (LCVR) of SEQ ID NO: 2 (hereinafter referred to as "mAb1"; US Patent Application Publication No. 20060275288 [Abbott Laboratories]) and are listed below:

Des-Ala-GLP1-mAb1: Des-Ala-GLP1 (SEQ ID NO: 5) fused to N-terminus of light chain of mAb1

Q-GLP1-mAb1: Q-GLP1 (SEQ ID NO: 6) fused to N-terminus of light chain of mAb1

A-GLP1-mAb1: A-GLP1 (SEQ ID NO: 7) fused to N-terminus of light chain of mAb1

Fusion proteins comprising mature GLP1 or GLP1 variant and an immunoglobulin Fc fragment were also generated and are listed below:

GLP1-hFc (SEQ ID NO: 9)
A-GLP1-hFc (SEQ ID NO: 10)
Q-GLP1-hFc (SEQ ID NO: 11)
Des-Ala-GLP1-hFc (SEQ ID NO: 12)
desH-GLP1-hFc (SEQ ID NO: 13)

Control Construct

Comparator: A GLP1 analogue having the amino acid sequence characteristics of LY2189265 fused to hIgG4 Fc domain (dulaglutide; Eli Lilly), as disclosed in Glaesner et al 2010 (Diabetes Metab. Res. Rev. 26: 287-296) was used as a comparator (SEQ ID NO: 14) in the following Examples.

Example 2: Luciferase Assay

The GLP1 fusion proteins were tested for their ability to stimulate cAMP production in a reporter cell line 293/FSC11/Cre-Luc that stably expresses the human GLP1 receptor together with a luciferase coding sequence under the control of a cre promoter that responds to cAMP.

For the luciferase bioassay, the 293/FSC11/Cre-Luc GLP1R stable cells were seeded into 96-well assay plates at 30,000 cells/well in OPTIMEM supplemented with 0.1% FBS and then incubated at 37° C. in 5% $CO_2$ overnight. The next day, to determine the dose response of test proteins, human GLP1 (Phoenix #028-13), des-Ala-GLP1-mAb1, Q-GLP1-mAb1, or A-GLP1-mAb1 were tested in the assay. All test compounds were purified proteins, except A-GLP1-mAb1 which was used directly from culture media after transient transfection of CHO cells with a vector encoding the modified antibody. The material in culture media was quantitated by ELISA. Test samples were added to cells at concentrations ranging from 0.02 pM to 100 nM.

After 5.5 hours or overnight incubation at 37° C. in 5% $CO_2$, OneGlo reagent (Promega, #E6051) was added to the samples and luciferase activity was then measured using a Victor X (Perkin Elmer) plate reader. The results were analyzed using nonlinear regression (three parameter) with Prism 6 software (GraphPad) to obtain $EC_{50}$ values.

As shown in the Table 1, the Q- and A-modified mAb1 antibody fusions show EC50 values of 204 pM and 312 pM, respectively, for GLP1R activation.

TABLE 1

EC50 for GLP1 fusion proteins

| GLP1 fusion proteins | EC50 |
|---|---|
| des-Ala-GLP1-mAb1 | 10 nM |
| Q-GLP1-mAb1 | 0.204 nM |
| A-GLP1-mAb1 | 0.312 nM |
| GLP1-hFc | 0.147 nM |
| A-GLP1-hFc | 120 nM |
| Q-GLP1-hFc | 135 nM |
| Des-Ala-GLP1-hFc | Not detectable |
| Des-H-GLP1-hFc | 2560 nM |
| Comparator | 0.059 nM |

The EC50 for des-Ala-GLP1-mAb1 was 10 nM. The EC50 for Q- and A-GLP1-hFc is only 135 nM and 120 nM, while the EC50 for Des A-GLP1-hFc is undetectable.

Example 3: Effect of Q-GLP1 Fused to GLP1R Antibody on Blood Glucose and Glucose Tolerance in GLP1R Humanized Mice The effect of Q-GLP1 fused to the N-terminus of the light chain of an anti-GLP1R antibody (Q-GLP1-mAb1) on blood glucose and glucose tolerance was determined in genetically engineered mice expressing the human GLP1R protein ("GLP1R humanized mice"). Thirty-one GLP1R humanized mice were divided into four groups of seven to eight animals. Each group received a single subcutaneous injection of isotype control, Q-GLP1-hFc, mAb1, or Q-GLP1-mAb1 at 194 nmol/kg. Mice were bled at fed condition on Days 0, 1, 4, 7, 11, 14, 16, 18, and 22 for blood glucose measurements. Mean±SEM of blood glucose levels at each time point was calculated for each group and shown in Table 2.

TABLE 2

Blood glucose levels

| | Time (days) | Isotype control | Q-GLP1-hFc | mAb1 | Q-GLP1-mAb1 |
|---|---|---|---|---|---|
| Blood Glucose (mg/dL) | 0 | 188 ± 6 | 188 ± 5 | 188 ± 6 | 186 ± 8 |
| | 1 | 185 ± 3 | 184 ± 8 | 193 ± 8 | 133 ± 4 |
| | 4 | 182 ± 9 | 193 ± 9 | 180 ± 7 | 128 ± 5 |
| | 7 | 187 ± 6 | 199 ± 9 | 178 ± 7 | 132 ± 4 |
| | 11 | 180 ± 4 | 192 ± 6 | 183 ± 8 | 152 ± 4 |
| | 14 | 174 ± 6 | 185 ± 8 | 184 ± 7 | 145 ± 4 |
| | 16 | 179 ± 6 | 193 ± 7 | 183 ± 7 | 156 ± 4 |
| | 18 | 172 ± 7 | 184 ± 8 | 161 ± 7 | 154 ± 6 |
| | 22 | 174 ± 6 | 188 ± 7 | 181 ± 9 | 171 ± 7 |

Oral glucose tolerance tests (oGTT) were performed on Day 3 and 9 after overnight fasting with blood glucose measurements at 0, 15, 30, 60, and 120 minutes after a bolus glucose gavarging. Mean±SEM of blood glucose levels at each time point and glucose area under curve (AUC) were calculated for each group and shown in Tables 3 and 4.

TABLE 3

Blood glucose levels and glucose AUC on day 3

| | Time (min) | Isotype control | Q-GLP1-hFc | mAb1 | Q-GLP1-mAb1 |
|---|---|---|---|---|---|
| Blood glucose (mg/dL) | 0 | 143 ± 6 | 147 ± 5 | 143 ± 8 | 111 ± 5 |
| | 15 | 242 ± 13 | 252 ± 19 | 233 ± 16 | 193 ± 11 |
| | 30 | 233 ± 9 | 235 ± 8 | 217 ± 8 | 160 ± 6 |
| | 60 | 187 ± 8 | 195 ± 7 | 200 ± 12 | 129 ± 4 |
| | 120 | 151 ± 7 | 160 ± 7 | 159 ± 10 | 115 ± 4 |
| Blood glucose AUC (mg/dL * 120 min) | | 22884 ± 594 | 23756 ± 681 | 23229 ± 959 | 16556 ± 386 |

TABLE 4

Blood glucose levels and glucose AUC on day 9

| | Time (min) | Isotype control | Q-GLP1-hFc | m Ab1 | Q-GLP1-mAb1 |
|---|---|---|---|---|---|
| Blood glucose (mg/dL) | 0 | 143 ± 4 | 151 ± 3 | 147 ± 5 | 116 ± 4 |
| | 15 | 281 ± 17 | 269 ± 15 | 253 ± 15 | 203 ± 13 |
| | 30 | 207 ± 5 | 228 ± 15 | 223 ± 14 | 167 ± 14 |
| | 60 | 200 ± 7 | 187 ± 5 | 207 ± 8 | 139 ± 10 |
| | 120 | 155 ± 5 | 173 ± 11 | 157 ± 6 | 131 ± 7 |
| Blood glucose AUC (mg/dL * 120 min) | | 23589 ± 610 | 23869 ± 795 | 23959 ± 696 | 17852 ± 920 |

A single administration of Q-GLP1-mAb1 in normoglycemic GLP1R humanized mice led to significant glucose reductions for 14 days, whereas Q-GLP1-hFc or mAb1 did not affect blood glucose levels (Table 2). Q-GLP1-mAb1 reduced fasting glucose levels and improved glucose tolerance on Day 3 and 9 in the mice, whereas Q-GLP1-hFc and mAb1 did not. These data suggest that Q-GLP1 or the mAb1 antibody alone does not change glycemic control, however, a fusion molecule of the two could exert glucose lowering effects that last for 2 weeks with a single injection in normoglycemic animals.

Example 4: Stability of GLP1 Variants

The stability of various GLP1 variants and fusion proteins was tested by incubating them with serum proteases and analyzing the cleaved peptides by mass spectrometry.

In a first experiment, half μg of each GLP1 fusion protein was added into 50 μL naïve mouse serum, respectively. The mixtures were then incubated at 37° C. for 6 hrs and 24 hrs, respectively. One μL serum mixtures at 0 min, 6 hr and 24 hr were loaded onto a Tris-Glycine gel.

In a second experiment, to further differentiate the stabilities, two μg of each GLP1 fusion protein was incubated with 500 ng of recombinant human DPP4 (R & D system) in PBS (pH 7.4) at 37° C. for 0 min, 1 hr, 4 hrs and 72 hrs, respectively. One fifth of the above mixture (equiv. 400 ng of construct) was loaded onto a Tris-Glycine gel.

For each experiment, the gel sections corresponding to each construct's molecular weight were excised and subject to in-gel trypsin digestion. The excised gel pieces were de-stained in 50:50 acetonitrile: $NH_4HCO_3$ (50 mM), reduced with 65 mM dithiothreitol (Sigma) at 37° C. for 30 min followed by alkylation with 135 mM iodoacetamide (Sigma) at room temperature in the dark for 30 min. Subsequently, proteins were digested overnight with sequencing grade modified porcine trypsin (Promega) at 37° C. Peptides were extracted twice with extraction buffer (50% ACN, 5% formic acid in H$_2$O). The extracted peptides from each band were dried to completion in SpeedVac and reconstituted with 0.1% tetrafluoroacetic acid (TFA) prior to nanoLC-MS/MS analysis.

The reconstituted peptide mixtures were separated by online reverse-phase (RP) nanoscale capillary liquid chromatography (Easy-nLC1000, Thermo Fisher Scientific) and analyzed by electrospray tandem mass spectrometry (Orbitrap Elite, Thermo Fisher Scientific). The peptide mixtures were injected onto a 75 µm inner diameter "PepMap RSLC" column (C18, 25 cm, 100 Å, 2 µm, Thermo Fisher Scientific) with a flow rate of 250 nL/min and subsequently eluted with 2% to 35% ACN in 0.1% formic acid in a 60-min gradient. The mass spectrometer was operated in data-dependent mode to automatically switch between MS and MS/MS acquisition. Survey full scan MS spectra (from m/z 350 to 2000) were acquired in the Orbitrap with a resolution of 120,000. The most intense ions (up to ten), were sequentially isolated for fragmentation in the hybrid ion trap using collision induced dissociation (CID) with a normalized collision energy of 35% at a target value of 5000. Target ions already selected for MS/MS were dynamically excluded for 30 s.

The MS and MS/MS peak lists were extracted and searched against an in-house protein database using ProteomeDiscoverer 1.4 (Thermo Fisher Scientific). All searches assumed trypsin digestion, and considered carboxymethylation of cysteine as a fixed modification and oxidation of methionine as a variable modification. A peptide mass tolerance of 10 ppm, MS/MS mass tolerance of 0.8 Da, and an allowance for up to 1 miss cleavage were used. The extracted ion areas were computed based on extracted ion chromatograms (XIC) using Thermo Xcaliber software (Thermo Fisher Scientific).

Results

To characterize each construct's susceptibility to serum enzyme cleavages, the intact peptide (N-terminal peptide), cleaved peptide (post-cleavage N-terminal peptide), and one internal reference peptide (a stable peptide unsusceptible to any modification in a construct) for each construct was monitored by nanoLC-MS/MS. A reduced ratio of the intact peptide vs. the reference peptide and concomitant increased ratio of the cleaved peptide vs. the reference peptide suggested enzyme-mediated cleavage of a construct over time.

Percent cleavage was calculated using the following formula: 100×area of cleaved peptide/(area of cleaved peptide+ area of uncleaved peptide)

GLP1-hFc and A-GLP1-hFc were cleaved completely by 6 hr, whereas desH-GLP1-hFc showed noticeable cleavage (2%) by 6 hr. Q-GLP1-hFc and Comparator did not show any cleavage after 24 hr incubation (Table 5).

TABLE 5

Percent cleavage of selected GLP1 receptor agonists

|  | Cleavage % in 6 hours | Cleavage % in 24 hours |
|---|---|---|
| GLP1-hFc | 100% | 100% |
| desH-GLP1-hFc | 2% | 5% |
| Q-GLP1-hFc | 0% | 0% |
| A-GLP1-hFc | 100% | 100% |
| Comparator | 0% | 0% |

To further differentiate the stabilities of Q-GLP1-hFc and Comparator, the two constructs were mixed with recombinant human DPP4, and the intact peptide (N-terminal peptide), cleaved peptide (post-cleavage N-terminal peptide), and one internal reference peptide (a stable peptide unsusceptible to any modification in a construct) for either construct was monitored by nanoLC-MS/MS.

TABLE 6

Stability of selected GLP1 receptor agonists to DPP4

|  | Cleavage % after 4 hours | Cleavage % after 72 hours |
|---|---|---|
| Q-GLP1-hFc | 0% | 0% |
| Comparator | 4% | 41% |

Comparator showed noticeable cleavage (4%) by 4 hours and over 40% cleavage by 72 hours (Table 6). By contrast, Q-GLP1-hFc did not exhibit any cleavage even after 72-hour incubation with DPP4 at 37° C.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of lowering blood sugar level in a subject in need thereof, wherein the method comprises administering to the subject a pharmaceutical composition comprising a therapeutically effective amount of a fusion protein consisting of a glucagon-like peptide 1 (GLP1) variant and a stabilizing domain, and wherein: (i) the GLP1 variant consists of SEQ ID NO: 6; (ii) the stabilizing domain is an antibody or antigen-binding fragment thereof that binds specifically to GLP1 receptor; and (iii) the fusion protein has enhanced resistance to proteolytic cleavage and/or enhanced blood glucose lowering ability.

2. The method of claim 1, wherein the subject has a disease or disorder selected from the group consisting of diabetes mellitus, obesity, insulin resistance, hypertension, dyslipidemia, Type 2 diabetes, Type 1 diabetes, pre-diabetes, cardiovascular disease, atherosclerosis, congestive heart failure, coronary heart disease, arteriosclerosis, peripheral artery disease, stroke, respiratory dysfunction, renal disease, fatty liver disease, non-alcoholic steatohepatitis (NASH), and metabolic syndrome.

3. The method of claim 1, wherein the pharmaceutical composition is administered in combination with a second therapeutic agent or therapy.

4. The method of claim 3, wherein the second therapeutic agent or therapy is selected from the group consisting of an insulin or insulin analogue, metformin, a thiazolidinedione, a sulfonylurea, a biguanide, chlorpropamide, a glinide, an alpha glucosidase inhibitor, nateglinide, a dipeptidyl peptidase 4 (DPP4) inhibitor, pramlintide, sitagliptin, bromocriptine, a sodium glucose cotransporter-2 (SGLT-2) inhibitor, canagliflozin, an anti-hypertensive drug, a statin, aspirin, dietary modification, exercise, and a dietary supplement.

5. The method of claim 1, wherein the pharmaceutical composition is administered subcutaneously, intravenously, intradermally, intraperitoneally, orally, or intramuscularly.

* * * * *

UNITED STATES PATENT AND TRADEMARK OFFICE
CERTIFICATE OF CORRECTION

| | | |
|---|---|---|
| PATENT NO. | : 11,779,633 B2 | Page 1 of 1 |
| APPLICATION NO. | : 17/332215 | |
| DATED | : October 10, 2023 | |
| INVENTOR(S) | : Yang Wei et al. | |

It is certified that error appears in the above-identified patent and that said Letters Patent is hereby corrected as shown below:

On the Title Page

Item (71) should read as follows:
(71) Applicant: Regeneron Pharmaceuticals, Inc.,
Tarrytown, NY (US)

Signed and Sealed this
Seventh Day of November, 2023

Katherine Kelly Vidal
*Director of the United States Patent and Trademark Office*